(12) United States Patent
Dryer et al.

(10) Patent No.: US 8,821,547 B2
(45) Date of Patent: Sep. 2, 2014

(54) SPINOUS PROCESS IMPLANT WITH A POST AND AN ENLARGED BOSS

(75) Inventors: Randall F. Dryer, Austin, TX (US); Greg C. Marik, Collierville, TN (US); Charles Schulte Sullivan, III, Germantown, TN (US); Steven D. DeRidder, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 960 days.

(21) Appl. No.: 12/916,761

(22) Filed: Nov. 1, 2010

(65) Prior Publication Data
US 2012/0109198 A1    May 3, 2012

(51) Int. Cl.
*A61B 17/70*    (2006.01)

(52) U.S. Cl.
CPC .................................. *A61B 17/7062* (2013.01)
USPC ........................................ 606/248; 606/249

(58) Field of Classification Search
USPC .................................. 606/71, 246, 248–249; 623/17.11–17.16
See application file for complete search history.

(56) References Cited

U.S. PATENT DOCUMENTS

| | | |
|---|---|---|
| 7,048,736 B2 | 5/2006 | Robinson et al. |
| 2001/0049529 A1 | 12/2001 | Cachia et al. |
| 2003/0040746 A1 | 2/2003 | Mitchell et al. |
| 2006/0064166 A1 | 3/2006 | Zucherman et al. |
| 2006/0235533 A1 | 10/2006 | Blain |
| 2006/0247640 A1 | 11/2006 | Blackwell et al. |
| 2006/0282079 A1 | 12/2006 | Labrom et al. |
| 2007/0093825 A1 | 4/2007 | Ferree et al. |
| 2007/0162005 A1 | 7/2007 | Peterson et al. |
| 2008/0183211 A1 | 7/2008 | Lamborne et al. |
| 2008/0183218 A1 | 7/2008 | Mueller et al. |
| 2009/0018658 A1 | 1/2009 | Garcia |
| 2011/0022090 A1* | 1/2011 | Gordon et al. ................ 606/249 |

\* cited by examiner

*Primary Examiner* — Pedro Philogene
*Assistant Examiner* — Christina Negrellirodrigue (57) ABSTRACT

A spinous process implant with two plates that are connected together with a post. The implant is configured for each plate to be positioned on outer lateral sides of spinous processes with the post extending through the interspinous space. One or both plates may be movable along the length of the post to accommodate different anatomies such as for relatively wide or thin spinous processes. The post includes an enlarged head at a first end to prevent the first plate from disassociating from the post in a first direction. The post also includes a boss at a second end to prevent the second plate from disassociating from the post in a second direction. Methods of attaching the implants to the spinous processes are also disclosed.

20 Claims, 6 Drawing Sheets

SPINOUS PROCESS IMPLANT WITH A POST AND AN ENLARGED BOSS

BACKGROUND

The present application is directed to devices and methods for stabilizing vertebral members, and more particularly, to implants to engage onto the spinous processes.

Vertebral members comprise a body, pedicles, laminae, and processes. The body includes sections on inferior and superior ends and has an hourglass shape with a thinner middle section and wider ends. Intervertebral discs are positioned between the bodies of adjacent vertebral members to permit flexion, extension, lateral bending, and rotation. The pedicles are two short rounded members that extend posteriorly from the body, and the laminae are two flattened members that extend medially from the pedicles. The processes are projections that serve as connection points for the ligaments and tendons. The processes include the articular processes, transverse processes, and the spinous process. Each vertebral member has four articular processes including two superior and two inferior processes. The superior processes of a first vertebral member join with the inferior processes of a second vertebral member to form facet joints. The facet joints work with the intervertebral discs to allow motion of the spine. The spinous process is a single member that extends posteriorly from the junction of the two lamina. The spinous process may act as a lever to effect motion of the vertebral member.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

One manner of correcting the damage is insertion of an implant onto the spinous processes. The implant may reduce or eliminate the pain and neurological deficit.

SUMMARY

The present application is directed to implants for attaching to spinous processes. The implant may include an elongated post with a first end, an opposing second end, and a shaft that extends between the first and second ends. A first plate may be attached to the first end of the post and sized to extend along a first lateral side of the spinous processes. A second plate may be sized to extend along a second lateral side of the spinous processes. The second plate may have an inner side that faces towards the spinous processes, an outer side that faces away from the spinous processes, and a bore that extends through the plate and receives the post with the second end of the post positioned outward beyond the outer side. The bore may have a larger cross-sectional size than the shaft for the second plate to be movable along the shaft. A boss may be positioned at the second end of the post and may be larger than the cross-sectional size of the bore to prevent the second plate from moving beyond the second end.

The application is also directed to methods of attaching an implant to spinous processes. The method may include positioning a first plate at a first end of a post, and may include sliding a second plate along the post and away from the first plate and increasing a distance between the plates. The second plate may include a bore that receives the post. The method may include contacting the second plate against an enlarged boss at a second end of the post and preventing the second plate from moving further away from the first plate. The method may include positioning the plates on opposing lateral sides of the spinous processes and the post within an interspinous space between the spinous processes. The method may include sliding the second plate away from the boss and towards the first plate and decreasing the distance between the plates with each of the plates contacting against the spinous processes. The second plate may also be secured to the post.

The various aspects of the various embodiments may be used alone or in any combination, as is desired.

DETAILED DESCRIPTION

The present application is directed to a spinous process implant with two plates that are connected together with a post. The implant is configured for each plate to be positioned on outer lateral sides of spinous processes with the post extending through the interspinous space. One or both plates may be movable along the length of the post to accommodate different anatomies such as for relatively wide or thin spinous processes. The post includes an enlarged head at a first end to prevent the first plate from disassociating from the post in a first direction. The post also includes a boss at a second end to prevent the second plate from disassociating from the post in a second direction.

Figure 1:
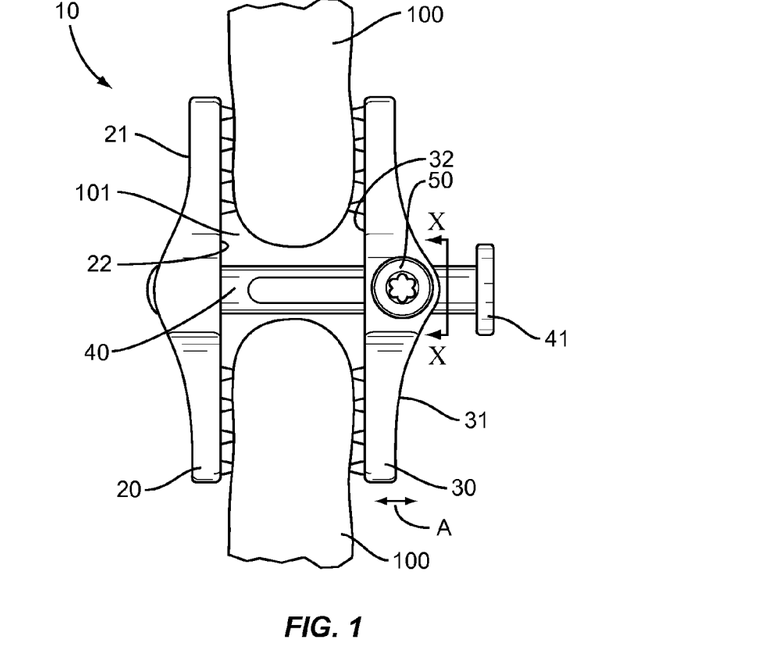
FIG. 1 is a rear side view of an implant attached to spinous processes according to one embodiment.

FIG. 1 is a rear view of the implant 10 secured to adjacent spinous processes 100. The implant 10 includes first and second plates 20, 30 secured to opposing outer lateral sides of the spinous processes 100. A post 40 connects the plates 20, 30 together and extends through the interspinous space 101 between the spinous processes 100. The second plate 30 can slide along the post 40 in the directions of arrow A to adjust a distance between the plates 20, 30 to accommodate the spinous processes 100. The post 40 includes a boss 41 at a second end to prevent removal of the second plate 30. A locking element 50 secures the second plate 30 to the post 40 at the desired longitudinal position.

Figure 2:
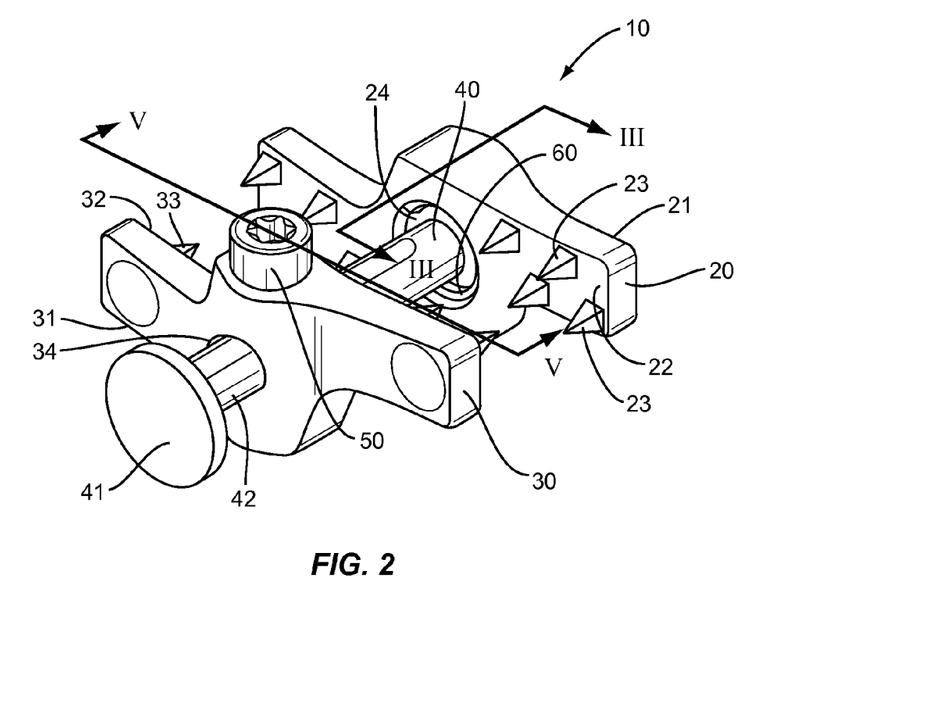
FIG. 2 is a perspective view of an implant according to one embodiment.

FIG. 2 illustrates the implant 10 prior to attachment to the spinous processes 100. The first plate 20 includes an outer side 21 that faces away from the spinous processes 100 when attached in a patient, and an inner side 22 that faces towards the spinous processes 100. Likewise, the second plate 30 includes an outer side 31 and an inner side 32. One or both plates 20, 30 may include teeth 23, 33 respectively that extend outward from the inner sides 22, 32. The teeth 23, 33 may extend along an entirety or a limited section of the plates 20, 30. The teeth 23, 33 may include a sharpened tip to engage with the spinous processes 100 to securely position the implant 10. The plates 20, may include the same or different shapes and sizes. FIGS. 1 and 2 include embodiments with the plates 20, 30 having substantially the same shape and size.

Figure 3:
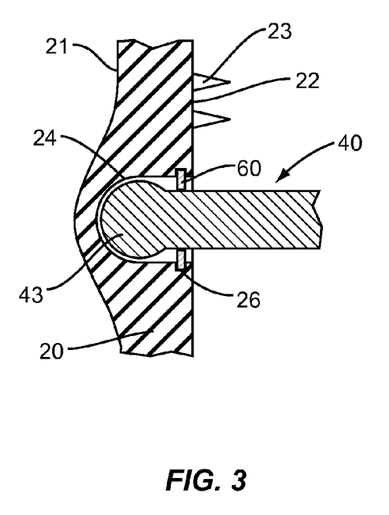
FIG. 3 is a sectional view cut along line III-III of FIG. 2 of a first end of a post in a receptacle according to one embodiment.

The first plate 20 includes a receptacle 24 to receive a head 43 of the post 40. FIG. 3 includes the receptacle 24 extending inward a limited distance from the inner side 22 and being sized to receive the head 43. The receptacle 24 may have a depth for the head 43 to be positioned within the interior of the plate 20 between the outer and inner sides 21, 22. The head 43 and receptacle 24 may be sized and shaped for the post 40 to pivot relative to the plate 20. FIG. 3 includes each of the head 23 and receptacle 24 having a rounded sectional shape for the post 40 to pivot within the plate 20.

A locking member 60 may be attached to the plate 20 to secure the head 43 within the receptacle 24. In one embodiment, the locking member 60 is positioned within a groove 26 in the plate 20. Other embodiments include the locking member 60 secured to the plate 20 by mechanical fasteners or adhesives. The locking member 60 includes an opening for the post 40 to extend outward from the receptacle 24. In one embodiment, the locking member 60 is a C-ring that fits within the groove 26.

Figure 4:
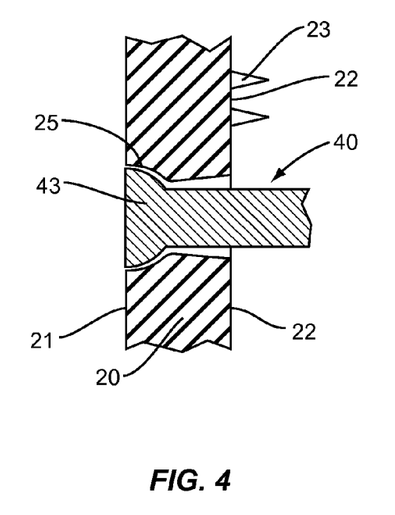
FIG. 4 is a sectional view similar to FIG. 3 of a first end of a post in a receptacle according to one embodiment.

The receptacle 24 may also extend completely through the first plate 20 as illustrated in FIG. 4. The receptacle 24 may include an enlarged recess 25 in the outer side 21 to receive the head 43 of the post 40. The depth of the recess 24 may allow for the head 43 to be positioned flush or recessed inward from the outer side 21. The shape of the post 40 and the receptacle 24 may allow for pivoting movement of the post 40 relative to the plate 20. In another embodiment (not illustrated), the first plate 20 and post 40 are constructed as a single piece. This may include the plate 20 and post 40 formed as a single unitary member.

The second plate 30 includes a bore 34 to receive the post 40. The bore 34 is sized relative to the post 40 for the plate 30 to be movable along the length of the post 40 for adjusting a distance from the first plate 20. The bore 34 may include various cross-sectional shapes and sizes depending upon the post 40. Examples include circular, rectangular, and irregular shapes. Each of the various bores 34 includes cross-sectional size.

Figure 5:
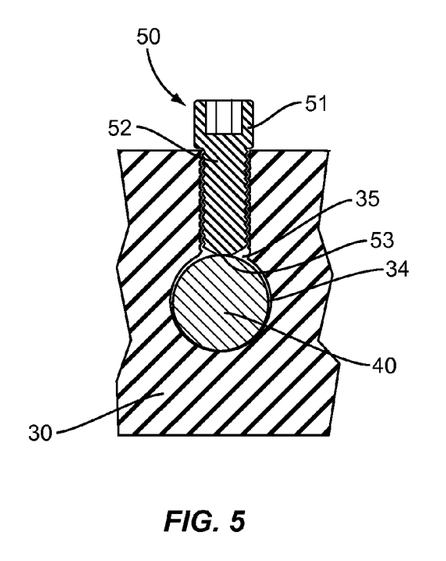
FIG. 5 is a sectional view cut along line V-V of FIG. 2 of a locking element engaging a post according to one embodiment.

As illustrated in FIG. 5, the plate 30 may also include a cavity 35 that extends inward from an exterior surface and intersects with the bore 34. The cavity 35 extends into the plate 30 at a transverse angle relative to the bore 34. In one embodiment, a longitudinal axis of the cavity 35 is perpendicular to a longitudinal axis of the bore 34. The locking element 50 is configured to fit within the bore 34 and engage the post 40. The locking element 50 includes a head 51 and an outwardly-extending shaft 52. The shaft 52 and cavity 35 may each be threaded to facilitate the positioning of the locking element 50 within the plate 30 and against the post 40. The shaft 52 further includes a tip 53 that contacts against the post 40. The tip 53 may be substantially flat, or may include a curved shape to increase an amount of contact with the post 40. The tip 53 may also include teeth or other like surface configurations to further facilitate the contact with the post 40. The post 40 may include a flat area along the perimeter to engage with the tip 53.

Figure 6:
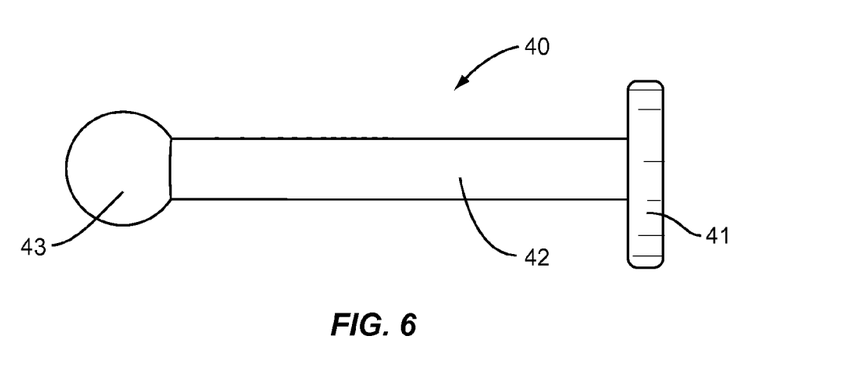
FIG. 6 is a side view of a post according to one embodiment.

The post 40 includes the head 43, shaft 42, and boss 41 as illustrated in FIG. 6. Each of the head 43 and boss 41 include a larger cross-sectional size than the shaft 42. The head 43 is sized to remain at the first plate 20, and the boss 41 is sized to remain outside of the second plate 30. The shaft 42 may be substantially straight as illustrated in FIG. 6, or may include a slight bend. The shaft 42 is sized to allow the second plate 30 to move along the length to adjust a distance from the first plate 20.

Figure 7:
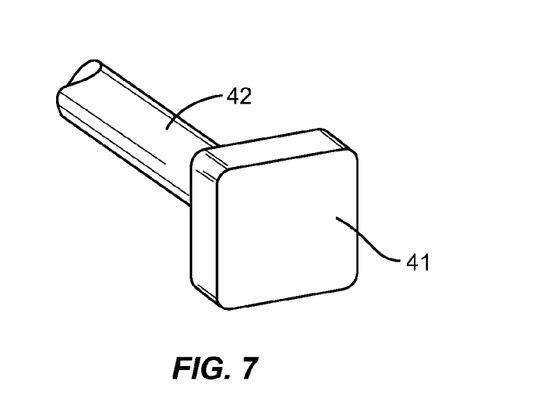
FIG. 7 is a perspective view of a boss on a post according to one embodiment.
Figure 8:
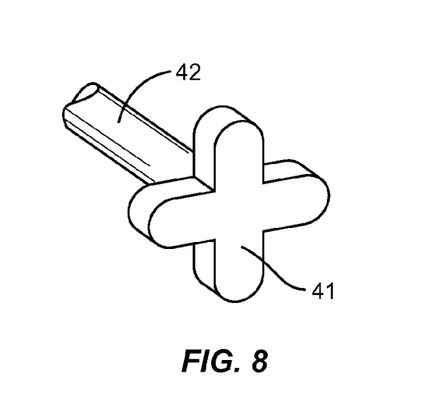
FIG. 8 is a perspective view of a boss on a post according to one embodiment.
Figure 9:
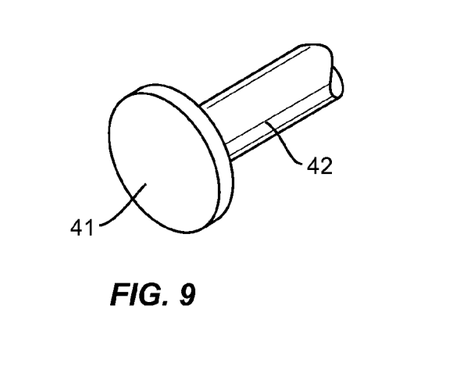
FIG. 9 is a perspective view of a boss on a post according to one embodiment.

The boss 41 is sized to prevent removal of the second plate 30 from the shaft 42. The boss 41 includes a larger size than the bore 34 to prevent the bore 34 from second plate 30 from passing over the boss 41 and becoming disassociated from the post 40. The boss 41 may include a variety of shapes and sizes, such as substantially rectangular shape as illustrated in FIG. 7, a cruciate shape as illustrated in FIG. 8, and a circular shape as illustrated in FIG. 9. Each of the shapes is larger than the corresponding bore 34.

Figure 10A:
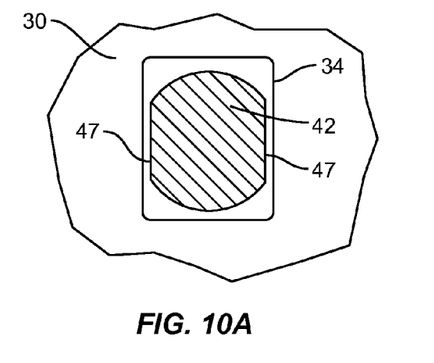
FIG. 10A is a sectional view cut along line X-X of FIG. 1 of a shaft and a bore according to one embodiment.
Figure 10B:
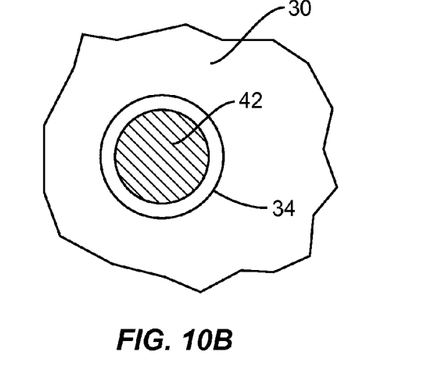
FIG. 10B is a sectional view cut along line X-X of FIG. 1 of a shaft and a bore according to one embodiment.
Figure 10C:
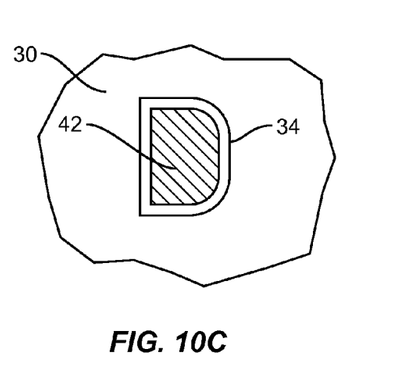
FIG. 10C is a sectional view cut along line X-X of FIG. 1 of a shaft and a bore according to one embodiment.

The shaft 42 and the bore 34 may include various sectional shapes to control the rotational orientation of the second plate 30 relative to the post 40. FIG. 10A includes the shaft 42 with a pair of flat sides 47 that align with flat sides of the bore 34 to prevent the plate 30 from rotating relative to the post 40. The cross-sectional sizes of the post 40 and bore 34 allow for movement of the plate 30 along the length of the post 40. Other shapes may also be provided that allow for movement along the length but prevent or limit rotational movement. FIG. 10B illustrates an embodiment with a circular sectional shape that may be used with a plate 30 having a bore 34 of a similar shape to allow for rotation of the plate 30 about the post 40. FIG. 10C includes the shaft 42 and the bore 34 having asymmetric shapes. These shapes provide for the plate 30 to have a specific orientation relative to the post 40.

The boss 41 may be removable from the shaft 42. Removal of the boss 41 may occur after the implant 10 is positioned within the patient and second plate 30 is secured to the post 40. The shaft 42 may include a joint 44 with a weakened section or a mechanical connection for removal of the boss 41.

The joint 44 may be weaker than the remainder of the shaft 42 and fracture upon the application of an external force on the boss 41. The external force may be substantially perpendicular to a longitudinal axis of the post 40. The external force may also be a torsional force applied to the boss 41.

Figure 11:
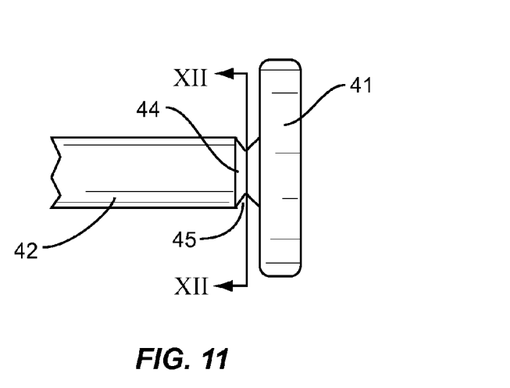
FIG. 11 is a side view of a joint positioned between a shaft and a boss according to one embodiment.
Figure 12A:
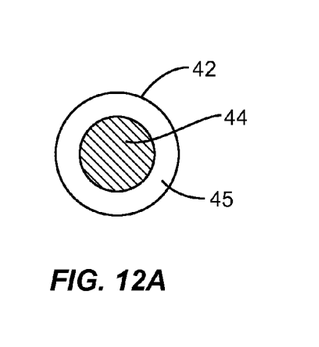
FIG. 12A is a sectional view cut along line XII-XII of FIG. 11 of a joint according to one embodiment.
Figure 12B:
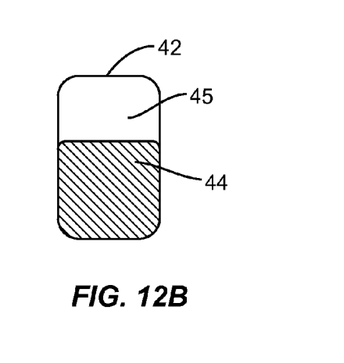
FIG. 12B is a sectional view cut along line XII-XII of FIG. 11 of a joint according to one embodiment.

One construction for a weakened joint 44 is illustrated in FIG. 11 and includes a notch 45 that extends around a portion or the entirety of the periphery of the shaft 42. The notch 45 causes the joint 44 to have a smaller cross-sectional area than the remainder of the shaft 42 causing a fracture to occur at the joint 44. FIG. 12A illustrates a notched joint 44 with a smaller cross-sectional area than the adjacent post 42. The notch 45 extends around the periphery of the shaft 42 in this embodiment. FIG. 12B includes a joint 44 with the notch 45 extending around a limited portion of the periphery of the shaft 42.

Figure 13:
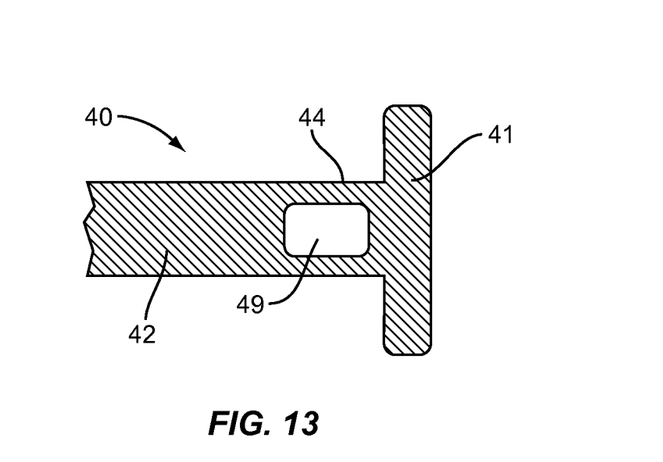
FIG. 13 is a longitudinal sectional view of a post with a joint and a boss according to one embodiment.

FIG. 13 includes the weakened joint 44 formed by a void 49 in the interior of the shaft 42. The void 49 weakens the joint 44 thus causing a fracture when an external force is applied to the boss 41. FIG. 13 includes the joint 44 having a single void 49, although other embodiments may include joints 44 with multiple voids 49.

Figure 14:
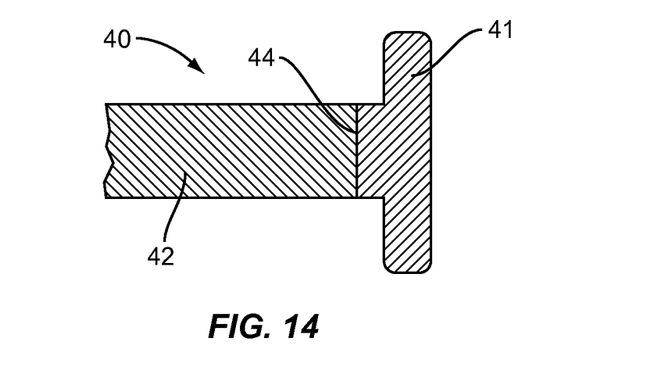
FIG. 14 is a longitudinal sectional view of a post with a joint and a boss according to one embodiment.

The weakened joint 44 may also be formed by the shaft 42 having an abutment face between different materials. FIG. 14 includes the shaft 42 and boss 41 constructed from different materials and secured together at the joint 44. This joint 44 is weaker than the remainder of the shaft 42 thus causing a fracture upon the application of an external force. The sections may be secured together by various techniques, including adhesives.

Figure 15:
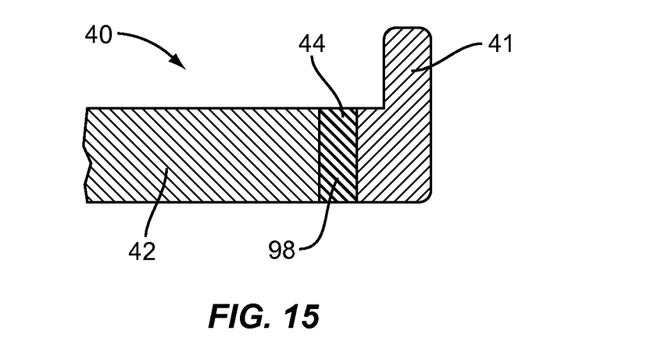
FIG. 15 is a longitudinal sectional view of a post with a joint and a boss according to one embodiment.

FIG. 15 includes the joint 44 formed by a weaker material 98 than that of the shaft 42 and the boss 41. The fracture may occur at the material 98.

The different aspects that form the weakened joint 44 may be used separately or in combination. For example, a joint 44 may include a notch 45 and a void 49, and a joint 44 may include a notch 45 positioned at a connection between sections constructed of different materials.

Figure 16:
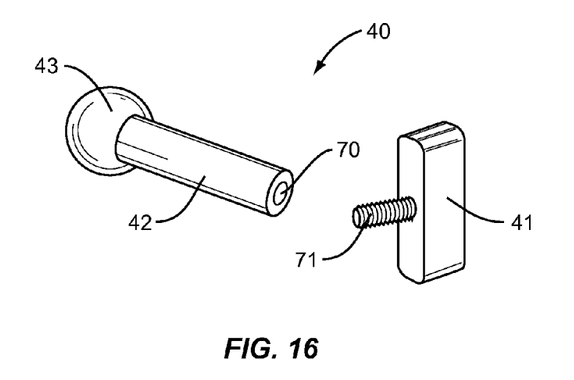
FIG. 16 is a perspective view of a joint with the boss separated from the shaft according to one embodiment.

The joint 44 may also include a mechanical connection that secures together the shaft 42 and the boss 41. FIG. 16 includes a mechanical connection featuring a receptacle 70 in the shaft 42 that receives a post 71 that extends outward from the boss 41. Each of the receptacle 70 and post 71 may be threaded to facilitate removal of the boss 41. FIG. 16 includes the aperture in the shaft 42 and the post 71 extending from the boss 41. The orientation may also be reversed with the shaft 42 including the post 71 and the boss 41 including the aperture 70.

Figure 17:
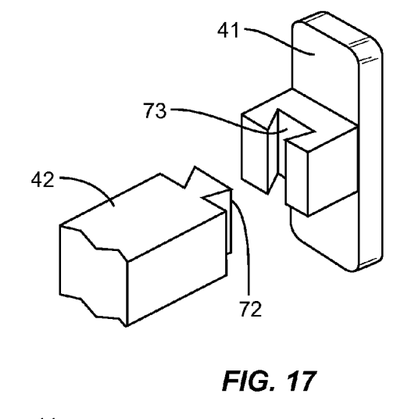
FIG. 17 is a perspective view of a joint with the boss separated from the shaft according to one embodiment.

Another mechanical connection is illustrated in FIG. 17 and includes an extension 72 on the shaft 42 and a corresponding receptacle 73 on the boss 41. The extension 72 is sized to fit within the receptacle 73 to attach the boss 41 to the shaft 42. In this embodiment, the extension 72 and receptacle 73 each include a dovetailed configuration. A ball-and-detent feature may also be included to further secure the boss 41 and shaft 42. Removal of the boss 41 may occur with a force applied substantially perpendicular to the longitudinal axis of the shaft 42 causing the boss 41 to slide out of the shaft 42. FIG. 17 includes the extension 72 on the shaft 42 and the receptacle 73 on the boss 41. The orientation may also be reversed.

Figure 18:
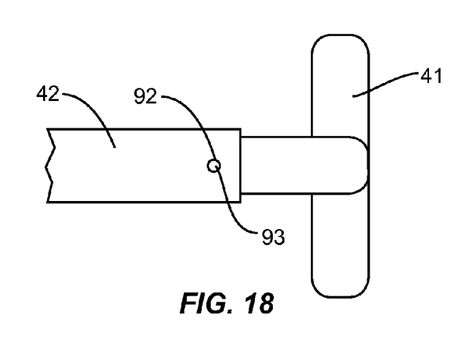
FIG. 18 is a side view of a joint with a boss attached to a shaft according to one embodiment.
Figure 19:
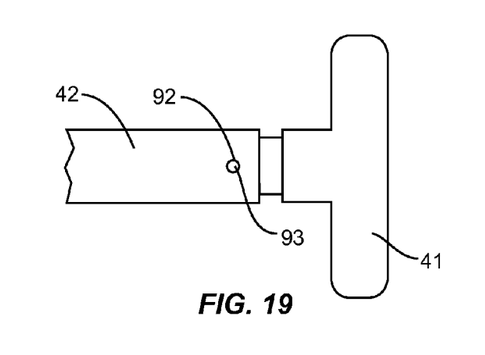
FIG. 19 is a side view of a joint with a boss attached to a shaft according to one embodiment.

FIG. 18 includes an embodiment with the boss 41 overlapping in a telescoping arrangement with the distal end of the shaft 42. The boss 41 and shaft 42 each include apertures 92 that align together and receive a fastener 93 to secure the boss 41 and shaft 42 together. The fastener 93 is removed from the apertures 92 for removal of the boss 41. FIG. 19 illustrates a similar embodiment with the shaft of the boss 41 being substantially equal in width to the shaft 42.

In use, the implant 10 is positioned in the patient with the first plate 20 on a first lateral side of the spinous processes 100 and the second plate 30 positioned on an opposing second lateral side of the spinous processes 100. The shaft 42 extends outward from the first plate 20 and through the interspinous space 101 and through the bore 34 in the second plate 30. In one embodiment, the second plate 30 is positioned on the shaft 42 prior to insertion into the patient (i.e., the complete implant 10 of the plates 20, 30 and post 40 are inserted as a single unit into the patient). In another embodiment, the implant 10 may be inserted into the patient as separate elements and attached together within the patient.

The second plate 30 may be moved along the shaft 42 away from the first plate 20 to accommodate the anatomy of the patient. The second plate 30 contacts against the boss 41 and is prevented from disassociating from the post 40. This prevents the plate 30 from potentially falling into the patient during the surgical process or otherwise becoming removed from the post 40 and requiring the surgeon to reconnect the second plate 30.

After the second plate 30 is moved away from the first plate 20 an adequate distance to accommodate the spinous processes 100, the second plate 30 is moved along the shaft 42 towards the first plate 20 and into contact with the lateral sides of the spinous processes 100. This includes the second plate 30 moving away from the boss 41 and along a length of the shaft 42. The plates 20, 30 may be moved together to apply a compressive force to the spinous processes 100. Once positioned the proper distance apart, the locking element 50 is engaged with the shaft 42 to maintain the spacing of the plates 20, 30.

With the second plate 30 secured to the shaft 42, the boss 41 may be no longer necessary. The boss 41 is separated from the shaft 42 by applying a force to the boss 41 and either fracturing the weakened joint 44 or disconnecting the mechanical connection. Once separated, the boss 41 can be removed from the patient.

A spacer may also be positioned around the shaft 42 between the first and second plates 20, 30. The spacer includes a central bore that receives the shaft 42. The spacer includes a first contact surface to contact against the first spinous process, and a second contact surface to contact against the second spinous process.

U.S. patent application Ser. No. 12/916,745 entitled Spinous Process Implant with Extended Post, filed on the same day of the present application, discloses an interspinous device with a pair of plates and a post, and is herein incorporated by reference in its entirety.

The implants 10 may be implanted within a living patient for the treatment of various spinal disorders. The implant 10 may also be implanted in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An implant for attaching to spinous processes comprising: an elongated post with a first end, an opposing second end, and a shaft that extends between the first and second ends; a first plate attached to the first end of the post and sized to extend along a first lateral side of the spinous processes; a second plate sized to extend along a second lateral side of the spinous processes, the second plate having an inner side that faces towards the spinous processes, an outer side that faces away from the spinous processes, and a bore that extends through and is completely contained within the plate and receives the post with the second end of the post positioned outward beyond the outer side, the bore having a larger cross-sectional size than the shaft for the second plate to be movable along the shaft; a locking element to secure the second plate to the shaft; and a boss positioned at the second end of the post, the boss being larger than the cross-sectional size of the bore to prevent the second plate from moving beyond the second end; the second plate being positioned away from the boss with the shaft between the second plate and the boss being exposed when the second plate is secured to the shaft and prevented from moving along the shaft and further comprising a joint positioned along the shaft in proximity to the boss to remove the boss from the shaft.

2. The device of claim 1, wherein the first end is larger than the cross-sectional size of the bore.

3. The device of claim 2, wherein the first end is positioned within a receptacle in the first plate and the post is pivotally attached to the first plate.

4. The device of claim 1, wherein the second plate includes a cavity that intersects with the bore, and the locking element extends through the cavity and contacts against the shaft to secure the second plate to the shaft.

5. The device of claim 1, wherein the joint includes a weakened section that is structurally weaker than a remainder of the shaft.

6. The device of claim 1, wherein the joint includes a mechanical connection with a first section connected to the boss and a second section connected to an end of a remainder of the shaft, the first and second sections mating together to attach the boss to the shaft.

7. The device of claim 1, wherein the boss includes cross-sectional shapes configured to control the rotational orientation of the second plate relative to the post.

8. The device of claim 1, wherein a spacer is positioned around the shaft between the first plate and the second plate, the spacer including a central bore that receives the shaft, the spacer including a first contact surface to contact against the first lateral side of the spinous processes, and a second contact surface to contact against the second lateral side of the spinous processes.

9. An implant for attaching to spinous processes comprising: first and second plates each with an inner side and an outer side, the first plate having a receptacle extending inward from the inner side and the second plate having a bore; a post with enlarged first and second ends and an intermediate shaft with a smaller cross-sectional size than the ends, the first end positioned in the receptacle in the first plate and the shaft extending through the bore in the second plate with the second end positioned outward beyond the outer side of the second plate opposite from the first plate; and a locking element to lock the second plate to the shaft at a desired distance away from the first plate; the bore of the second plate including a cross-sectional size that is larger than the shaft for the second plate to be movable along the shaft between the first and second ends and smaller than the second end to maintain the second plate along the shaft between the second end and the first plate, wherein the joint includes a notch that extends into the shaft with the joint having a smaller cross-sectional size than a remainder of the shaft.

10. The implant of claim 9, wherein the joint includes a void positioned within an interior of the shaft.

11. The implant of claim 9, wherein the joint includes an abutment face between the shaft constructed from a first material and the second end constructed from a different second material.

12. The implant of claim 9, wherein the joint is constructed from a different material than the shaft.

13. The device of claim 12, wherein the joint is constructed from a weaker material than the shaft, the weaker material configured to fracture.

14. The device of claim 9, wherein the joint includes a threaded extension that mates with a threaded aperture.

15. The device of claim 9, wherein the second plate includes a cavity that intersects with the bore and the locking element extends through the cavity and contacts against the shaft to secure the second plate to the shaft.

16. A method of attaching an implant to spinous processes comprising: positioning a first plate at a first end of a post; sliding a second plate along the post and away from the first plate and increasing a distance between the plates, the second plate including a bore that receives the post; contacting the second plate against an enlarged boss at a second end of the post and preventing the second plate from moving further away from the first plate; positioning the plates on opposing lateral sides of the spinous processes and the post within an interspinous space between the spinous processes; sliding the second plate away from the boss and towards the first plate and decreasing the distance between the plates with each of the plates contacting against the spinous processes; and securing the second plate to the post, wherein securing the second plate to the post comprises moving a fastener through a cavity in the second plate and into contact with the post.

17. The method of claim 16, further comprising positioning the boss away from the interspinous space.

18. The method of claim 16, further comprising positioning the first end of the post within a receptacle in the first plate with the first end positioned within an interior of the first plate between inner and outer sides.

19. The method of claim 16, further comprising removing the boss from the post after the second plate is secured to the post.

20. The method of claim 16, further comprising moving the plates against the lateral sides of the spinous processes and applying a compressive force to the spinous processes.

* * * * *